United States Patent
Toda et al.

(10) Patent No.: US 8,350,050 B2
(45) Date of Patent: Jan. 8, 2013

(54) BIS-(1(2)H-TETRAZOL-5-YL) AMINE AND PRODUCTION METHOD THEREFOR

(75) Inventors: Toshiyuki Toda, Takasago (JP); Toru Kofukuda, Takasago (JP)

(73) Assignee: Toyo Boseki Kabushiki Kaisha, Osaka-shi, Osaka (JP)

( * ) Notice: Subject to any disclaimer, the term of this patent is extended or adjusted under 35 U.S.C. 154(b) by 0 days.

(21) Appl. No.: 13/183,064

(22) Filed: Jul. 14, 2011

(65) Prior Publication Data

US 2012/0004419 A1    Jan. 5, 2012

Related U.S. Application Data (62) Division of application No. 12/705,989, filed on Feb. 16, 2010, now abandoned.

(60) Provisional application No. 61/153,011, filed on Feb. 17, 2009.

(51) Int. Cl.
*C07D 257/04* (2006.01)

(52) U.S. Cl. ....................................................... 548/251

(58) Field of Classification Search ................... 514/381; 548/251
See application file for complete search history.

(56) References Cited

U.S. PATENT DOCUMENTS

2007/0084531 A1 *  4/2007  Halpin et al. ................... 149/24

* cited by examiner

*Primary Examiner* — Shawquia Young
(74) *Attorney, Agent, or Firm* — Leydig, Voit & Mayer, Ltd.

(57) ABSTRACT

High-quality bis-(1(2)H-tetrazol-5-yl)amine and a method for easily, safely, and inexpensively producing the compound are provided. The method for producing bis-(1(2)H-tetrazol-5-yl)amine includes the steps of heating to 50 to 120° C. a solution mixture in which a necessary amount of an azide salt and a dicyanamide salt in an amount corresponding to 1 to 80 wt % of a necessary amount are added to a solvent, adding an acid in an amount of 1.54 to 2.22 chemical equivalents of the dicyanamide salt in the solution mixture to carry out a reaction at 50 to 120° C., and then adding an acid and a dicyanamide salt solution in which the remaining dicyanamide salt is dissolved in a solvent to promote the reaction. Bis-(1(2)H-tetrazol-5-yl)amine is obtained according to the production method.

1 Claim, 8 Drawing Sheets

| PKNO | TIME | AREA | HEIGHT | CONC |
|---|---|---|---|---|
| 1 | 2.567 | 2581 | 454 | 0.0409 |
| 2 | 3.463 | 22993 | 3107 | 0.3644 |
| 3 | 3.647 | 3893 | 577 | 0.0617 |
| 4 | 3.924 | 120223 | 16221 | 1.9051 |
| 5 | 4.222 | 21980 | 2591 | 0.3483 |
| 6 | 4.721 | 25006 | 2391 | 0.3963 |
| 7 | 5.017 | 6095 | 625 | 0.0966 |
| 8 | 5.776 | 1612 | 204 | 0.0255 |
| 9 | 6.267 | 3222 | 348 | 0.0511 |
| 10 | 6.803 | 1498 | 172 | 0.0237 |
| 11 | 7.376 | 8904 | 635 | 0.1411 |
| 12 | 7.997 | 5980956 | 526433 | 94.7788 |
| 13 | 10.067 | 6551 | 552 | 0.1038 |
| 14 | 16.037 | 49519 | 2555 | 0.7847 |
| 15 | 17.692 | 8985 | 464 | 0.1424 |
| 16 | 19.611 | 37104 | 1670 | 0.588 |
| 17 | 26.064 | 9315 | 305 | 0.1476 |
| | TOTAL | 6310436 | 559305 | 100 |

| PKNO | TIME | AREA | HEIGHT | CONC |
|---|---|---|---|---|
| 1 | 2.533 | 2502 | 237 | 0.0756 |
| 2 | 3.464 | 5094 | 706 | 0.154 |
| 4 | 3.921 | 5336 | 520 | 0.1613 |
| 5 | 4.218 | 3463 | 523 | 0.1047 |
| 7 | 5.024 | 1385 | 148 | 0.0419 |
| 8 | 6.27 | 1190 | 145 | 0.036 |
| 9 | 7.52 | 2098 | 208 | 0.0634 |
| 10 | 8.031 | 3281120 | 301871 | 99.1814 |
| 11 | 10.096 | 4128 | 350 | 0.1248 |
| 12 | 15.908 | 1884 | 111 | 0.0569 |
| TOTAL | | 3308200 | 304820 | 100 |

| PKNO | TIME | AREA | HEIGHT | CONC |
|---|---|---|---|---|
| 1 | 3.221 | 3922 | 614 | 0.0587 |
| 4 | 4.952 | 1780 | 231 | 0.0266 |
| 5 | 5.128 | 3375 | 369 | 0.0505 |
| 6 | 6.06 | 3633 | 363 | 0.0543 |
| 7 | 8.472 | 842 | 104 | 0.0126 |
| 8 | 8.977 | 6658846 | 728985 | 99.6044 |
| 9 | 10.991 | 1433 | 174 | 0.0214 |
| 10 | 11.578 | 1281 | 109 | 0.0192 |
| 12 | 14.211 | 8030 | 869 | 0.1201 |
| 14 | 19.927 | 2149 | 215 | 0.0321 |
|  | TOTAL | 6685291 | 732034 | 100 |

| PKNO | TIME | AREA | HEIGHT | CONC |
|---|---|---|---|---|
| 1 | 3.688 | 1506 | 312 | 0.0291 |
| 2 | 5.001 | 45745 | 4602 | 0.8838 |
| 3 | 5.555 | 87264 | 8538 | 1.6859 |
| 4 | 6.627 | 4458 | 385 | 0.0861 |
| 5 | 7.226 | 8667 | 680 | 0.1674 |
| 6 | 7.633 | 4129 | 258 | 0.0798 |
| 7 | 8.167 | 4943404 | 410161 | 95.5066 |
| 8 | 9.607 | 21350 | 1485 | 0.4125 |
| 9 | 9.903 | 8911 | 693 | 0.1722 |
| 10 | 14.359 | 45919 | 2512 | 0.8872 |
| 11 | 19.369 | 2947 | 148 | 0.0569 |
| 12 | 22.535 | 1682 | 146 | 0.0325 |
|  | TOTAL | 5175982 | 429920 | 100 |

| PKNO | TIME | AREA | HEIGHT | CONC |
|---|---|---|---|---|
| 1 | 2.561 | 1709 | 288 | 0.0308 |
| 2 | 2.673 | 1527 | 231 | 0.0275 |
| 4 | 3.469 | 6842 | 889 | 0.1232 |
| 5 | 3.65 | 3350 | 465 | 0.0603 |
| 6 | 3.917 | 8378 | 790 | 0.1509 |
| 7 | 4.179 | 8096 | 1099 | 0.1458 |
| 8 | 4.607 | 1031 | 147 | 0.0186 |
| 9 | 5.012 | 3668 | 454 | 0.0661 |
| 10 | 5.407 | 1073 | 134 | 0.0193 |
| 11 | 6.01 | 1832 | 184 | 0.033 |
| 12 | 6.388 | 3540 | 326 | 0.0637 |
| 13 | 7.39 | 5478276 | 509239 | 98.6636 |
| 14 | 8.255 | 14464 | 1222 | 0.2605 |
| 15 | 9.226 | 8864 | 669 | 0.1596 |
| 16 | 14.043 | 1828 | 115 | 0.0329 |
| 17 | 17.204 | 4681 | 234 | 0.0843 |
| 18 | 21.43 | 3322 | 152 | 0.0598 |
|  | TOTAL | 5552478 | 516639 | 100 |

BIS-(1(2)H-TETRAZOL-5-YL) AMINE AND PRODUCTION METHOD THEREFOR

CROSS REFERENCE TO CORRESPONDING APPLICATIONS

This application is a division of the non-provisional application Ser. No. 12/705,989 filed Feb. 16, 2010 now abandoned entitled BIS-(1(2)H-TETRAZOL-5-YL)AMINE AND PRODUCTION METHOD THEREOF which claims a priority to U.S. 61/153,011, filed Feb. 17, 2009 by applicants Toshiyuki TODA and Toru Kofukuda (both of Takasago Japan) and entitled BIS-(1(2)H-TETRAZOL-5-YL)AMINE AND PRODUCTION METHOD THEREOF, the contents of which is incorporated by reference in its entirety.

TECHNICAL FIELD

The present invention relates to bis-(1(2)H-tetrazol-5-yl)amine produced using an azide salt and a dicyanamide salt and to a production method therefor.

BACKGROUND ART

A bis-(1(2)H-tetrazol-5-yl)amine compound is useful as a gas generant, and a known production method uses an azide salt and a dicyanamide salt (for example, see Non-Patent Literature 1 and Patent Literatures 1 to 5).

In the production method described in Non-Patent Literature 1, a reaction is carried out under reflux for 23 hours using trimethylammonium chloride as an acid in an aqueous solvent, and then a treatment with hydrochloric acid is performed, thereby giving bis-(1(2)H-tetrazol-5-yl)amine monohydrate in a yield of 67%.

In the production method described in Patent Literature 1, a reaction is carried out under reflux for 48 hours using boric acid in a large excess in an aqueous solvent, and then a treatment with hydrochloric acid is performed, thereby giving bis-(1(2)H-tetrazol-5-yl)amine anhydrate in a yield of 80.3%.

In the production method described in Patent Literature 2, a reaction is carried out at 100 to 150°C. for 5 to 10 hours using an ammonium halide such as ammonium chloride as an acid in an aprotic solvent such as N,N-dimethylformamide, and then a treatment with hydrochloric acid is performed, thereby giving bis-(1(2)H-tetrazol-5-yl)amine monohydrate in a yield of 80 to 90%.

In the production method described in Patent Literature 3, a reaction is carried out at 95 to 105° C. for 24 hours using a protic acid such as hydrochloric acid and a metal chloride such as manganese chloride in water or a water-miscible solvent, the suspended solids of the metal salt are filtered off, and then a treatment with a protonic acid such as hydrochloric acid is performed, thereby giving bis-(1(2)H-tetrazol-5-yl) amine monohydrate in a yield of 80 to 90%.

In the production method described in Patent Literature 4, an acid having a pKa less than 2 is gradually mixed (usually for 12 to 24 hours) with a reaction solution at 65°C. or greater (desirably under reflux) in an aqueous solvent so as to maintain a high pH to keep the hydrazoic acid within the system. After the reaction, a treatment with a protonic acid such as hydrochloric acid is performed, thereby giving bis-(1(2)H-tetrazol-5-yl)amine monohydrate in a yield of about 86%.

In the production method described in Patent Literature 5, an acid of having a pKa of 3 to 9 is mixed with a reaction solution at 65° C. or greater (desirably under reflux) in an aqueous solvent, and after the reaction, the reaction solution is acidified so as to have a pH less than 3, thereby giving a bis-(1(2)H-tetrazol-5-yl)amine compound.

Citation List

Non-Patent Literature 1: "Journal of Organic Chemistry", 1964, Vol. 29, pp. 650-660
Patent Literature 1: WO 95/18802
Patent Literature 2: JP 2004-67544 A
Patent Literature 3: JP 2004-323392 A
Patent Literature 4: US 2003/0060634 A
Patent Literature 5: U.S. Pat. No. 5,468,866

Problems to Be Solved By the Invention

The above-described conventional production methods, however, have the following disadvantages.

The production method described in Non-Patent Literature 1 uses expensive trimethylammonium and generates triammonium azide, which is sublimable and carries a risk of explosion.

The production method described in Patent Literature 1 requires a reaction time as long as 48 hours and uses boric acid. It is difficult to thermally dispose of boric acid.

The production method described in Patent Literature 2 performs the reaction using only an organic solvent, involving a high solvent cost and a troublesome post-treatment, resulting in a high production cost. Moreover, ammonium azide, which is sublimable and carries a risk of explosion, is generated.

The production method described in Patent Literature 3 uses a manganese salt that cannot be readily removed, thereby requiring a troublesome post-treatment and thus resulting in a high production cost.

The production method described in Patent Literature 4 requires a long period of time for the dropwise addition of a strong acid, resulting in a high production cost, and the dropwise addition of acid at high temperatures results in a high hydrogen azide concentration in the gaseous phase and the resulting product is of a poor quality. Moreover, the product is obtained only as a crystalline monohydrate, and high temperatures are required to convert it into an anhydrate. Furthermore, once exposed to a humidity of 10% or greater, the anhydrate is promptly converted back into the monohydrate.

The production method described in Patent Literature 5 uses an acid having a pKa of 3 to 9 and therefore the reaction proceeds slowly, requiring the reaction to be carried out for a long period of time. In addition, even after a reaction carried out for a long period of time, a product having a purity of 99.0% or greater is not obtained.

SUMMARY OF THE INVENTION

The present invention was conceived in light of these situations, and an object of the invention is to provide high-quality bis-(1(2)H-tetrazol-5-yl)amine and a method for easily, safely, and inexpensively producing the compound.

Means for Solving the Problems

One mole of a dicyanamide salt reacts with 2 moles of an azide salt and 2 moles of an acid and, via several intermediates, eventually forms 1 mole of a bis-(1(2)H-tetrazol-5-yl) amine metal salt and 1 mole of an acid.

That is, in the initial reaction stage where intermediates are generated, 1 mol of a dicyanamide salt reacts with 2 mol of an azide salt and 2 mol of an acid. However, from the reaction stage where 1 mol of a bis-(1(2)H-tetrazol-5-yl)amine metal salt and 1 mol of an acid are generated onwards, the amount of acid starts to become excessive due to this acid generation.

The use of the acid that becomes excessive during the reaction allows the reaction of 1 mol of a dicyanamide salt to proceed with 2 mol of an azide salt and 1 mol of a starting acid, giving 1 mol of a bis-(1(2)H-tetrazol-5-yl)amine metal salt.

However, if an acid is not present in a sufficient amount from the initial reaction stage, the reaction barely proceeds and an impurity resulting from an intermediate is generated in large amounts. In contrast, if a dicyanamide salt is not present in a sufficient amount, hydrogen azide may be generated.

Figure 1:
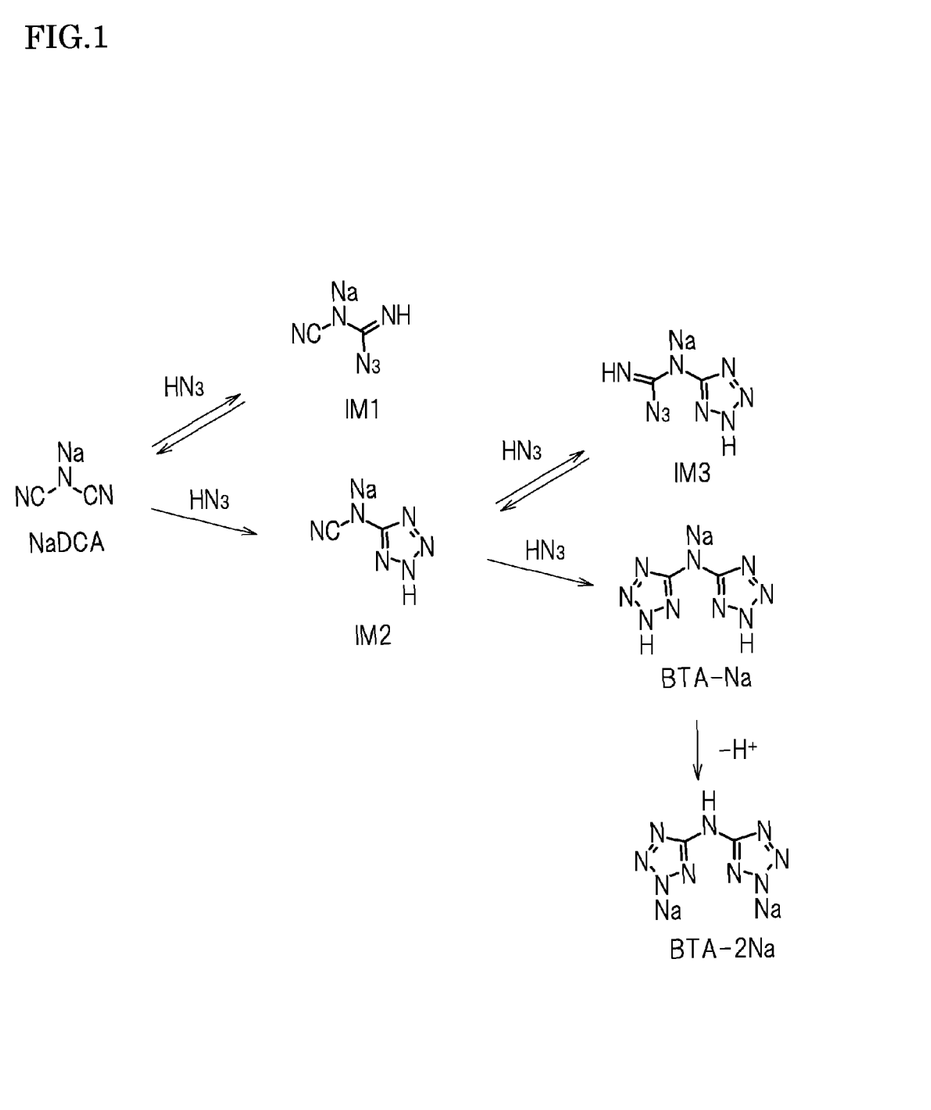
FIG. 1 is a reaction scheme showing the reaction process according to the method for producing bis-(1(2)H-tetrazol-5-yl)amine of the present invention.

To describe more specifically, as shown in FIG. 1, the production of a bis-(1(2)H-tetrazol-5-yl)amine metal salt is attained via the generation of several intermediates, namely IM1, IM2, and IM3. While the bis-(1(2)H-tetrazol-5-yl) amine metal salt can be stably present within the reaction system, the dicyanamide salt and the intermediates IM1 and 1M2 are poorly stable. This tendency becomes more pronounced when the pH is low.

It is necessary to suppress the decomposition of the intermediates IM1 and IM2 to enhance the quality of the bis-(1(2)H-tetrazol-5-yl)amine metal salt, and therefore it is necessary to:

1. maintain a high pH during the reaction, and
2. keep the concentrations of the starting materials and the intermediates IM1 and IM2 in the reaction system low.

Firstly, an acid is used in an amount as little as possible to keep the pH high.

While 2 mol of H+ is needed to form the tetrazole rings of the bis-(1(2)H-tetrazol-5-yl)amine metal salt, 1 mol of 1+ is released once the two tetrazole rings are formed (this may be because BTA-1Na is an acid stronger than NaN3).

Therefore, unless the released H+ is used in the reaction, the acidity of the system is increased as the reaction proceeds (the pH is decreased), thereby promoting the decomposition of the starting materials and the intermediates.

Therefore, the dropwise addition of the starting dicyanamide salt in divided amounts is a technique for forming the second tetrazole ring with the minimum amount of acid (equimolar relative to the dicyanamide salt) and for promptly converting the dicyanamide salt added in divided amounts into a bis-(1(2)H-tetrazol-5-yl)amine metal salt using the released H+.

If the reaction is carried out using a dicyanamide salt not in divided amounts and the minimum amount of an acid (equimolar relative to the dicyanamide salt), the pH of the reaction system is high, but the intermediate IM2, which has one tetrazole ring, is generated in a high concentration.

In such a reaction system, not only is the concentration of the unstable intermediate IM2 high and the quality of the desired product thus deteriorated, but also it takes a relatively long period of time to form a bis-(1(2)H-tetrazol-5-yl)amine metal salt due to the low concentration of the intermediate IM3.

The inventors, having conducted extensive research, found that a high-quality bis-(1(2)H-tetrazol-5-yl)amine metal salt can be obtained by starting a reaction using a portion of the necessary amount of a dicyanamide salt and by controlling the amount of a dicyanamide salt added or the amounts of a dicyanamide salt and an acid added thereafter according to the progress of the reaction so as to promote the reaction, and thus arrived at the present invention.

That is, to address the above-described problems, the method for producing bis-(1(2)H-tetrazol-5-yl)amine of the present invention includes the steps of heating to 50 to 120° C. a solution mixture in which the necessary amount of an azide salt and a dicyanamide salt in an amount corresponding to 1 to 80 wt % of the necessary amount are added to a solvent, adding an acid in an amount of 1.54 to 2.22 chemical equivalents of the dicyanamide salt in the solution mixture to carry out a reaction at 50 to 120° C., and then adding an acid and a dicyanamide salt solution in which the remaining dicyanamide salt is dissolved in a solvent to promote the reaction.

Examples of dicyanamide salts for use in the present invention include alkali metal salts, alkaline earth metal salts, and ammonium salts, and sodium dicyanamide is preferable.

Examples of azide salts for use in the present invention include alkali metal salts and alkaline earth metal salts, and sodium azide is preferable. The amount of azide salt is preferably in a range of 1.90 to 2.20 mol, and in particular 2.0 to 2.1 mol, per mol of the dicyanamide salt.

Examples of solvents for use in the present invention include water and water-miscible solvents such as aprotic polar solvents, N-substituted lactamic solvents, alcohols, and ethers, as well as mixtures of such solvents. Among such solvents, examples of aprotic polar solvents include N,N-dimethylformamide, N,N-diethylformamide, N,N-diisopropylformamide, N,N-dimethylacetamide, N,N-diethylacetamide, N,N-diisopropylacetamide, N,N-dimethylpropionamide, and N,N-diethylpropionamide. Examples of N-substituted lactamic solvents include N-methylpyrrolidone and N-ethylpyrrolidone. Examples of alcohols include methanol, ethanol, and isopropanol. Examples of ethers include tetrahydrofuran, dioxane, methylcellosolve, and ethylcellosolve. Such solvents may be used singly or as a mixture of two or more. Among such solvents, it is preferable to use water as a solvent to inexpensively produce the desired product. In this case, a water-miscible solvent may be added. The amount of solvent is usually in a range of 1 to 100 times, preferably 5 to 20 times, as much in weight as that of dicyanamide salt.

Examples of acids for use in the present invention include inorganic acids such as hydrochloric acid, sulfuric acid, nitric acid, phosphoric acid and perchloric acid, and organic acids such as formic acid, acetic acid, propionic acid, methanesulfonic acid, toluenesulfonic acid, trifluoroacetic acid and trifluoromethanesulfonic acid. Acetic acid, hydrochloric acid, and sulfuric acid are preferable in terms of availability and cost on an industrial scale, and acetic acid is particularly preferable in terms of safety. Additives such as amines or amine salts are not added to such acids. The amount of acid is in a range of 1.0 to 1.2 chemical equivalents per mole of the dicyanamide salt. Therefore, the amount of acid is in a range of 1.0 to 1.2 mol in the case of a monovalent acid, and 0.5 to 0.6 mol in the case of a divalent acid, per mole of dicyanamide salt.

Next, the production method shall be described.

First, the entire amount of an azide salt necessary in a reaction, a dicyanamide salt in an amount corresponding to 1 to 80 wt % of the amount necessary in the reaction, a solvent, and an acid in an amount of 1.54 to 2.22 chemical equivalents of the dicyanamide salt that is present in the 1 to 80 wt % amount are mixed and reacted at 50 to 120° C.

In this regard, if a dicyanamide salt, an azide salt, a solvent, and an acid are mixed as 4 separate ingredients, the order of mixing the ingredients is not particularly limited. For example, the acid may be added to a solution mixture of the dicyanamide salt, the azide salt and the solvent, or a solution mixture of the azide salt and the acid may be added to a dicyanamide salt solution in which the dicyanamide salt is dissolved in the solvent. In the latter case, the solution mixture may be added to the dicyanamide salt solution at 50 to 120° C. over 30 minutes to 12 hours. Meanwhile, the acid may be added to the solution mixture over such a long period of time similar to that mentioned above, or the entire amount of the acid may be added at once at a specific temperature, or half the amount may be added at a low temperature, heating may be carried out, and then the other half may be added. In the case of performing mixing in this manner, it is preferably performed under vigorous stirring. As to the temperature-time relationship during mixing, high temperature conditions carry risks and therefore mixing needs to be performed over a long period of time, while low temperature conditions allow mixing to be accomplished in a short period of time. From the operation time viewpoint, performing mixing at low temperatures in a short period of time may be considered preferable, but the rate of intermediate generation is low at low temperatures, requiring an additional acid and impairing the yield. In contrast, the rate of intermediate generation is high at high temperatures, but impurities are generated in addition to the intermediates and mixing needs to be performed over a long period of time. Therefore, the temperature and the time for mixing are determined depending on which of factors such as operation time, safety, yield, or purity are prioritized.

The dicyanamide salt is used in an amount 1 to 80 wt %, and preferably 50 to 80 wt %, of the amount necessary for reaction. If the dicyanamide salt is added in an amount less than 1 wt %, controlling the addition of the remaining 99 wt % is troublesome. If the dicyanamide salt is added in an amount exceeding 80 wt % of the amount necessary for reaction, the dicyanamide salt concentration in the reaction system is high, and thus impurities resulting from the dicyanamide salt and reaction intermediates are likely to be generated.

The acid is used in an amount of 1.54 to 2.22 chemical equivalents of the dicyanamide salt present in the 1 to 80 wt % amount. If the amount of acid is less than 1.54 chemical equivalents, the acid present in the initial reaction stage is insufficient, and the reaction barely proceeds. If the amount exceeds 2.22 chemical equivalents, the acid is excessive and hydrogen azide is likely to be generated.

In the next step, an acid and a dicyanamide salt solution in which the remaining dicyanamide salt is dissolved in a solvent are added to promote the reaction.

At this time, when to add the acid and the dicyanamide salt solution is determined as follows.

(1) The reaction solution is regularly sampled, and the addition of the acid and the dicyanamide salt solution is controlled such that the amount of dicyanamide salt remaining in the reaction solution is 0.1 to 3 wt % in reference to the area percentage obtained by liquid chromatographic analysis. Insofar as the amount of dicyanamide salt in the reaction solution is within the range of 0.1 to 3 wt %, the rate, order, and other factors of adding the acid and the dicyanamide salt solution are not particularly limited. When the amount of dicyanamide salt is less than 0.1 wt %, an excessive amount of acid is present and hydrogen azide is likely to be generated. When the amount of dicyanamide salt exceeds 3 wt %, the amount of acid is likely to be insufficient and the reaction is likely to barely proceed, making it difficult to complete the reaction, and impurities resulting from reaction intermediates are likely to be generated.

(2) If the reaction temperature is from 50 to 100° C., a pH meter can be used. Thus, while controlling the acid such that the pH is 6 to 9, the reaction is promoted by the addition of the acid and the dicyanamide salt solution. Insofar as the pH is within the range of 6 to 9, the rate, order, and other factors of adding the acid and the dicyanamide salt solution are not particularly limited. If the pH exceeds 9, the acid is likely to be insufficient and the progress of the reaction is likely to be inhibited. Meanwhile, if the pH is less than 6, hydrogen azide may be generated.

(3) If the entire amount of acid necessary to carry out the reaction is used in the previous step and only a dicyanamide salt solution is added in this step, the reaction can be controlled by adding the dicyanamide salt solution according to reaction curve data constructed in advance based on the reaction times of the dicyanamide salt solution at various temperatures. A specific example is the data presented in FIG. 2 that are obtained in Example 1 below. In this case, neither liquid chromatography nor a pH meter is used, and thus efficient production can be attained when the desired product is repetitively produced on a large scale.

As described above, a reaction is started using a dicyanamide salt in an amount corresponding to 1 to 80 wt % of the necessary amount, and then a dicyanamide salt and an acid (in some cases, a dicyanamide salt only) are added in divided and controlled amounts, thereby allowing the acid that is generated during the reaction to be effectively used to construct a favorable reaction environment. It is thus possible to produce a bis-(1(2)H-tetrazol-5-yl)amine metal salt compound that enables bis-(1(2)H-tetrazol-5-yl)amine ammonium salt having a high purity of 99.0 wt % or greater as determined on a weight basis according to the area percentage obtained by liquid chromatographic analysis to be obtained.

The bis-(1(2)H-tetrazol-5-yl)amine metal salt compound obtained in this stage has a purity of 94.0 area % or greater and does not have a peak accounting for 0.1 area % or greater within a relative retention time starting at 1.08 and ending at 1.20 assuming that the retention time to the main peak is 1 according to the area percentage obtained by HPLC analysis. A peak indicating an impurity derived from an unstable starting material or intermediate appears within the relative retention time starting at 1.08 and ending at 1.20 assuming that the retention time to the main peak is 1. Therefore, an impurity concentration of less than 0.1 area % as determined by the area percentage within this retention time indicates the presence of a bis-(1(2)H-tetrazol-5-yl)amine metal salt compound from which a high-quality bis-(1(2)H-tetrazol-5-yl) amine ammonium salt can be obtained.

Note that the HPLC analysis conditions include detection with UV220 nm, a column of Inertsil ODS-3 (4.6 mm ID.times.250 mm), a column bath temperature of 40° C., a mobile phase of water/acetonitrile/phosphoric acid in a ratio of 800/200/0.1, a mobile phase flow rate of 0.7 mL/min, and an amount of sample injected of 10 .mu.L (loop). The relative retention time starting at 1.08 and ending at 1.20 assuming that the retention time to the main peak is 1 has been determined in consideration of every possible error of measurement, and the peaks of the aforementioned impurities do not appear outside this range.

The conditions of HPLC analysis are not particularly limited to those described above insofar as the conditions allow the bis-(1(2)H-tetrazol-5-yl)amine metal salt compound, the dicyanamide salt, and each reaction intermediate to be distinguished for a quantitative analysis thereof and various HPLC analysis conditions may be adopted.

The bis-(1(2)H-tetrazol-5-yl)amine metal salt compound thus obtained is heat-treated at 75° C. or greater to complete the reaction, and a second acid solution is added thereto to form bis-(1(2)H-tetrazol-5-yl)amine anhydrate and/or monohydrate.

The heat treatment is carried out at 75° C. or greater and preferably 90° C. or greater. The heat treatment is carried out for 10 to 48 hours and preferably 10 to 30 hours. Although the reaction proceeds at a temperature below 75° C., the reaction rate is low and the reaction may not complete even after a long period of time.

The second acid solution is preferably of the same type of acid used in the method for producing the reaction intermediate described above, and a different type of acid may be used as well.

The addition of the second acid may be carried out while the reaction intermediate is heated during the heat treatment to 75° C. or greater, or may be added after the heat treatment is terminated and the intermediate is cooled to a specific temperature.

Controlling the temperature of the reaction intermediate at the time of adding the acid enables a monohydrate and an anhydrate to be selectively prepared. That is, controlling the temperature of the reaction intermediate to less than 70° C. enables bis-(1(2)H-tetrazol-5-yl)amine monohydrate to be mostly prepared. Meanwhile, controlling the temperature of the reaction intermediate to 70° C. or greater at the time of adding the acid enables bis-(1(2)H-tetrazol-5-yl)amine anhydrate to be mostly prepared. The dropwise addition of the acid is performed over the course of 2 hours or longer, and desirably 4 to 12 hours, to complete the reaction in a short period of time. Moreover, the acid is added until the pH reaches 3 or less to complete the reaction to enhance the yield.

The bis-(1(2)H-tetrazol-5-yl)amine anhydrate and/or monohydrate obtained at this stage has a purity of 99.0 area % or greater and does not have a peak accounting for 0.1 area % or greater within a relative retention time starting at 1.08 and ending at 1.20 assuming that the retention time to the main peak is 1 according to the area percentage obtained by HPLC analysis. A peak indicating an impurity derived from an unstable starting material or intermediate appears within the relative retention time starting at 1.08 and ending at 1.20 assuming that the retention time to the main peak is 1. Therefore, an impurity concentration of less than 0.1 area % as determined by the area percentage within this retention time indicates the presence of bis-(1(2)H-tetrazol-5-yl)amine anhydrate and/or monohydrate from which high-quality bis-(1(2)H-tetrazol-5-yl)amine ammonium salt can be obtained.

Note that the HPLC analysis conditions include detection with UV220 nm, a column of Inertsil ODS-3 (4.6 mm ID.times.250 mm), a column bath temperature of 40° C., a mobile phase of water/acetonitrile/phosphoric acid in a ratio of 800/200/0.1, a mobile phase flow rate of 0.7 mL/min, and an amount of sample injected of 10 .mu.L (loop). The relative retention time starting at 1.08 and ending at 1.20 assuming that the retention time to the main peak is 1 has been determined in consideration of every possible error of measurement, and the peaks of the aforementioned impurities do not appear outside this range.

The conditions of HPLC analysis are not particularly limited to those described above insofar as the conditions allow the bis-(1(2)H-tetrazol-5-yl)amine anhydrate and/or monohydrate, the dicyanamide salt, and each reaction intermediate to be distinguished for a quantitative analysis thereof, and various HPLC analysis conditions may be adopted.

The bis-(1(2)H-tetrazol-5-yl)amine anhydrate and/or monohydrate can be generated as bis-(1(2)H-tetrazol-5-yl) amine ammonium salt by controlling the pH through the dropwise addition of an amine.

The bis-(1(2)H-tetrazol-5-yl)amine ammonium salt obtained at this stage has a purity of 99.0 wt % or greater as determined on a weight basis and does not show a peak accounting for 0.1 wt % or greater as determined on a weight basis within a relative retention time starting at 2.17 and ending at 2.24 assuming that the retention time to the main peak is 1 according to the area percentage obtained by HPLC analysis. A peak indicating an impurity derived from an unstable starting material or impurity appears within the relative retention time starting at 2.17 and ending at 2.24 assuming that the retention time to the main peak is 1. Therefore, an impurity concentration of less than 0.1 wt % as determined on a weight basis according to the area percentage within this retention time indicates the presence of high-quality bis-(1(2)H-tetrazol-5-yl)amine ammonium salt.

Note that the HPLC analysis conditions include detection with UV220 nm, a column of Inertsil ODS-3 having 4.6 mm ID.times.250 mm, a column bath temperature of 30° C., a mobile phase (solution A: 0.1% phosphoric acid solution/acetonitrile/methanol in a ratio of 950/25/25, and solution B: 0.1% phosphoric acid solution/acetonitrile in a ratio of 400/600), a gradient program (0-30 minutes: 100-50% solution A, 0-50% solution B, and 30-60 minutes: 50% solution A, 50% solution B), a mobile phase flow rate of 1.0 mL/min, and an amount of a sample injected of 20 μL (loop). The relative retention time starting at 2.17 and ending at 2.24 assuming that the retention time to the main peak is 1 has been determined in consideration of every possible error of measurement, and the peaks of the aforementioned impurities do not appear outside this range.

The conditions of HPLC analysis are not specifically limited to those described above insofar as the conditions allow the bis-(1(2)H-tetrazol-5-yl)amine salt, the dicyanamide salt, and each reaction intermediate to be distinguished and quantitatively analyzed, and various HPLC analysis conditions may be adopted.

Effects of the Invention

As described above, the present invention allows a reaction to safely and efficiently proceed because a solution mixture in which the necessary amount of an azide salt and a dicyanamide salt in an amount corresponding to 1 to 80 wt % of the necessary amount are added to a solvent is heated to 50 to 120° C., an acid is added in an amount of 1.54 to 2.22 chemical equivalents of the dicyanamide salt in the solution mixture to carry out a reaction at 50 to 120° C., and then an acid and a dicyanamide salt solution in which the remaining dicyanamide salt is dissolved in a solvent are added to promote the reaction. Moreover, the present invention reduces the impurities generated during the reaction process and allows bis-(1(2)H-tetrazole 5-yl)amine ammonium salt having a high purity of 99.0 wt % or greater to be obtained.

BRIEF DESCRIPTION OF THE DRAWINGS

FIG. 5(a) is a chromatogram of the bis-(1(2)H-tetrazol-5-yl)amine ammonium salt of Example 6 according to the method for producing bis-(1(2)H-tetrazol-5-y0amine of the present invention, and FIG. 5(b) is analytical data of the chromatogram.

DETAILED DESCRIPTION OF THE PREFERRED EMBODIMENTS

The present invention shall be described in detail below by way of examples although the present invention is not limited to the examples.

Example 1

11.57 g of sodium dicyanamide (hereinafter simply referred to as "NaDCA", 0.13 mol, 65 wt % of the entire NaDCA used in the reaction), 26.39 g of sodium azide (0.406 mol, 2.03 times the molar amount of the entire NaDCA used in the reaction), and 90 mL of water were introduced into a 300 mL flask and heated while stirring until the internal temperature reached 100° C.

While the internal temperature was maintained at 100° C., 16.81 g of a 63% sulfuric acid solution (0.108 mol, 1.08 times the chemical equivalents of the entire NaDCA used in the reaction) was added over the course of 3 hours.

While the internal temperature was maintained at 100° C., an aqueous NaDCA solution in which remaining 6.24 g of NaDCA (0.07 mol, 35 wt % of the entire NaDCA used in the reaction) had been dissolved in 30 mL of water was added dropwise over the course of 26 hours.

At this time, the rate of the dropwise addition was controlled so as to maintain the NaDCA content of the reaction solution at 1 wt % or less according to HPLC analysis.

Figure 2:
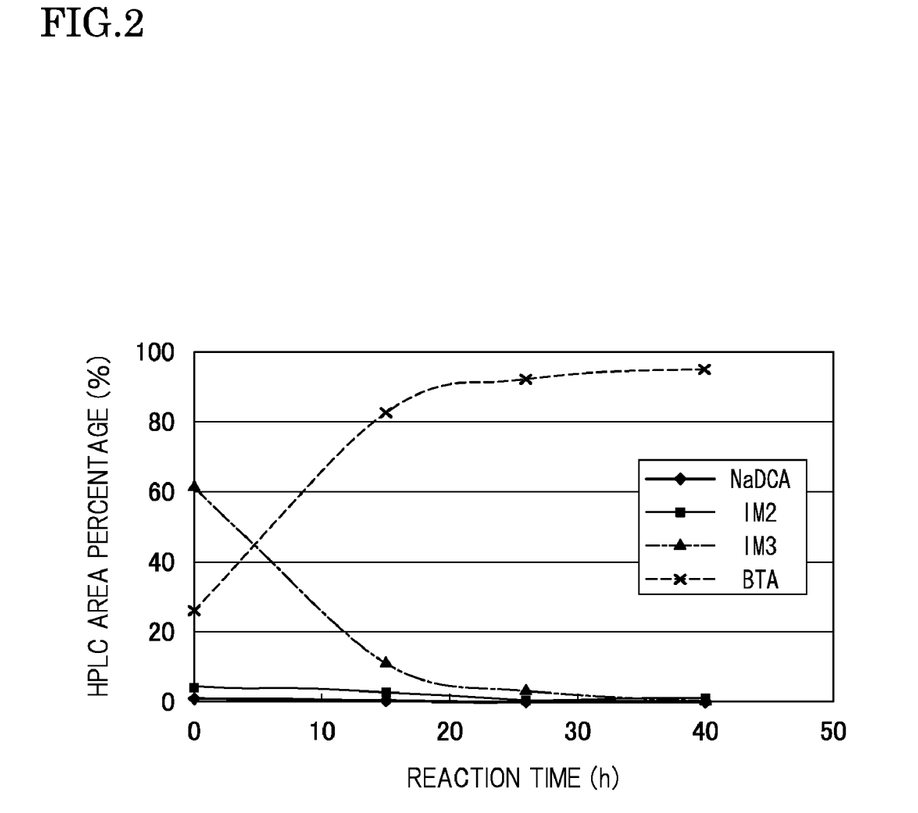
FIG. 2 shows the change over time in the amounts of a dicyanamide salt and intermediates generated according to the method for producing bis-(1(2)H-tetrazol-5-yl)amine of the present invention.

The reaction was further promoted by stirring at 100° C. for 10 hours, and the internal temperature was then lowered to near room temperature. FIG. 2 shows the results of HPLC analysis showing the change over time in the proportions of specific components eluted out.

75 mL of water and 31.45 g (0.202 mol) of a 63% sulfuric acid solution were added to the reaction solution for crystallization, and 2.0 g of a 40% aqueous sodium nitrite solution was then added to decompose unreacted hydrogen azide. Crystals were filtered off at about 25.degree. C., thereby giving about 42 g of wet bis-(1(2)H-tetrazol-5-yl)amine.

This compound was vacuum-dried at 60° C., thereby giving 30.50 g of bis-(1(2)H-tetrazol-5-yl)amine having an HPLC purity of 99.4 area % in a yield of 89.2%.

Example 2

Monohydrate 11.57 g of NaDCA (0.13 mol, 65 wt % of the entire NaDCA used in the reaction), 26.39 g of sodium azide (0.406 mol, 2.03 times the molar amount of the entire NaDCA used in the reaction), and 90 mL of water were introduced into a 300 mL flask and heated while stirring until the internal temperature reached 100° C.

While the internal temperature was maintained at 100.degree. C., 14.28 g of 90% acetic acid (0.214 mol, 1.07 times the chemical equivalents of the entire NaDCA used in the reaction) was added over the course of 3 hours.

While the internal temperature was maintained at 100° C., an aqueous NaDCA solution in which remaining 6.24 g of NaDCA (0.07 mol, 35 wt % of the entire NaDCA used in the reaction) had been dissolved in 30 mL of water was added dropwise over the course of 26 hours.

At this time, the rate of the dropwise addition was controlled so as to maintain the NaDCA content of the reaction solution at 1 wt % or less according to HPLC analysis.

The reaction was further promoted by stirring at 100° C. for 10 hours, and the internal temperature was then lowered to near room temperature.

75 mL of water was added, and while the internal temperature was maintained at 70° C., 48.3 g (0.31 mol) of a 63% sulfuric acid solution was added for crystallization, and 2.0 g of a 40% aqueous sodium nitrite solution was then added to decompose unreacted hydrogen azide. Crystals were filtered off at about 25° C. and dried, thereby giving 30.9 g of bis-(1(2)H-tetrazol-5-yl)amine monohydrate having an HPLC purity of 99.1 area % in a yield of 90.3%.

Example 3

Anhydrate 11.57 g of NaDCA (0.13 mol, 65 wt % of the entire NaDCA used in the reaction), 26.39 g of sodium azide (0.406 mol, 2.03 times the molar amount of the entire NaDCA used in the reaction), and 90 mL of water were introduced into a 300 mL flask and heated while stirring until the internal temperature reached 100° C.

While the internal temperature was maintained at 100° C., 14.28 g of 90% acetic acid (0.214 mol, 1.07 times the chemical equivalents of the entire NaDCA used in the reaction) was added over the course of 3 hours.

While the internal temperature was maintained at 100° C., an aqueous NaDCA solution in which remaining 6.24 g of NaDCA (0.07 mol, 35 wt % of the entire NaDCA used in the reaction) had been dissolved in 30 mL of water was added dropwise over the course of 26 hours.

At this time, the rate of the dropwise addition was controlled so as to maintain the NaDCA content of the reaction solution at 1 wt % or less according to HPLC analysis.

The reaction was further promoted by stirring at 100° C. for 10 hours, and the internal temperature was then lowered to near room temperature.

75 mL of water was added, and while the internal temperature was maintained at 90° C., 48.3 g (0.31 mol) of a 63% sulfuric acid solution was added for crystallization, and 2.0 g of a 40% aqueous sodium nitrite solution was then added to decompose unreacted hydrogen azide. Crystals were filtered off at about 25.degree. C. and dried, thereby giving 27.4 g of bis-(1(2)H-tetrazol-5-yl)amine anhydrate having an HPLC purity of 99.2 area % in a yield of 89.4%.

Example 4

11.57 g of NaDCA (0.13 mol, 65 wt % of the entire NaDCA used in the reaction), 26.39 g of sodium azide (0.406 mol, 2.03 times the molar amount of the entire NaDCA used in the reaction), and 90 mL of water were introduced into a 300 mL flask and heated while stirring until the internal temperature reached 60° C.

While the internal temperature was maintained at 60° C., 16.81 g of 63% sulfuric acid (0.108 mol, 1.08 times the chemical equivalents of the entire NaDCA used in the reaction) was added over the course of 3 hours.

The internal temperature was increased to 100° C., and while the internal temperature was maintained at 100° C., an aqueous NaDCA solution in which 6.24 g of NaDCA (0.07 mol, 35 wt % of the entire NaDCA used in the reaction) had been dissolved in 30 mL of water was added dropwise over the course of 26 hours.

At this time, the rate of the dropwise addition was controlled so as to maintain the NaDCA content of the reaction solution at 1 wt % or less according to HPLC analysis.

The reaction was further promoted by stirring at 100° C. for 10 hours, and the internal temperature was then lowered to near room temperature.

75 mL of water and 31.45 g (0.202 mol) of a 63% sulfuric acid solution were added for crystallization, and 2.0 g of a 40% aqueous sodium nitrite solution was then added to decompose unreacted hydrogen azide. Crystals were filtered off at about 25° C., thereby giving about 42 g of wet bis-(1(2)H-tetrazol-5-yl)amine.

This compound was vacuum-dried at 60° C., thereby giving 30.20 g of bis-(1(2)H-tetrazol-5-yl)amine having an HPLC purity of 99.2 area % in a yield of 88.3%.

Example 5

11.57 g of NaDCA (0.13 mol, 65 wt % of the entire NaDCA used in the reaction), 26.39 g of sodium azide (0.406 mol, 2.03 times the molar amount of the entire NaDCA used in the reaction), and 90 mL of water were introduced into a 200 mL flask and heated while stirring until the internal temperature reached 100° C.

While the internal temperature was maintained at 100° C., 12.5 g of acetic acid (0.208 mol, 1.04 times the chemical equivalents of the entire NaDCA used in the reaction) was added over the course of 2 hours.

While the internal temperature was maintained at 100° C., an aqueous NaDCA solution in which remaining 6.24 g of NaDCA (0.07 mol, 35 wt % of the entire NaDCA used in the reaction) had been dissolved in 30 mL of water was added dropwise over the course of 20 hours.

At this time, the rate of the dropwise addition of the aqueous NaDCA solution was changed every hour. Specifically, the rate of dropwise addition was gradually reduced so as to be 4.5 mL/hr for the 1st hour, 3.9 mL/hr for the 2nd hour, 3.4 mL/hr for the 3rd hour, 3.0 mL/hr for the 4th hour, and so on.

The rate of the dropwise addition was controlled so as to maintain the NaDCA content of the reaction solution at 1 wt % or less according to HPLC analysis.

The reaction was further promoted by stirring at 100° C. for 10 hours, and the internal temperature was then lowered to near room temperature.

75 mL of water and 48.3 g (0.31 mol) of a 63% sulfuric acid solution were added for crystallization, and 2.0 g of a 40% aqueous sodium nitrite solution was then added to decompose unreacted hydrogen azide. Crystals were filtered off at about 25.degree. C., thereby giving about 42 g of wet bis-(1(2)H-tetrazol-5-yl)amine.

The entire amount of the wet bis-(1(2)H-tetrazol-5-yl)amine and 150 mL of water were introduced into a 200 mL flask to form a suspension. The pH was controlled so as to be 4 to 6 by adding a 28% ammonia solution. The suspension was cooled to 10° C. or lower and then subjected to filtration, thereby giving about 35 g of wet bis-(1(2)H-tetrazol-5-yl)amine ammonium salt.

This compound was vacuum-dried at 60° C., thereby giving 28.5 g of bis-(1(2)H-tetrazol-5-yl)amine ammonium salt having a purity of 99.7 wt % as determined on a weight basis from the results of HPLC analysis in a yield of 84%.

Example 6

0.18 g of NaDCA (0.002 mol, 1 wt % of the entire NaDCA used in the reaction), 26.39 g of sodium azide (0.406 mol, 2.03 times the molar amount of the entire NaDCA used in the reaction), and 90 mL of water were introduced into a 200 mL flask and heated while stirring until the internal temperature reached 100° C.

52.96 g of 20% sulfuric acid (1.08 times the chemical equivalents of the entire NaDCA used in the reaction) was added dropwise over the course of 35 hours.

40 minutes after the beginning of the dropwise addition of 20% sulfuric acid, an aqueous NaDCA solution in which 17.63 g of NaDCA (0.198 mol, 99 wt % of the entire NaDCA used in the reaction) had been dissolved in 85 mL of water was added dropwise over the course of 34 hours while the internal temperature was maintained at 100° C.

At this time, the rate of the dropwise addition was controlled so as to maintain the NaDCA content of the reaction solution at 1 wt % or less according to HPLC analysis. The HPLC conditions included detection with UV220 nm, a column of Inertsil ODS-3 (4.6 mm ID.times.250 mm), a column bath temperature of 40° C., a mobile phase of water/acetonitrile/phosphoric acid in a ratio of 800/200/0.1, a mobile phase flow rate of 0.7 mL/min, and an amount of sample injected of 10 µL (loop).

The reaction was further promoted by stirring at 100° C. for 10 hours, and the internal temperature was then lowered to near room temperature.

Figure 3:
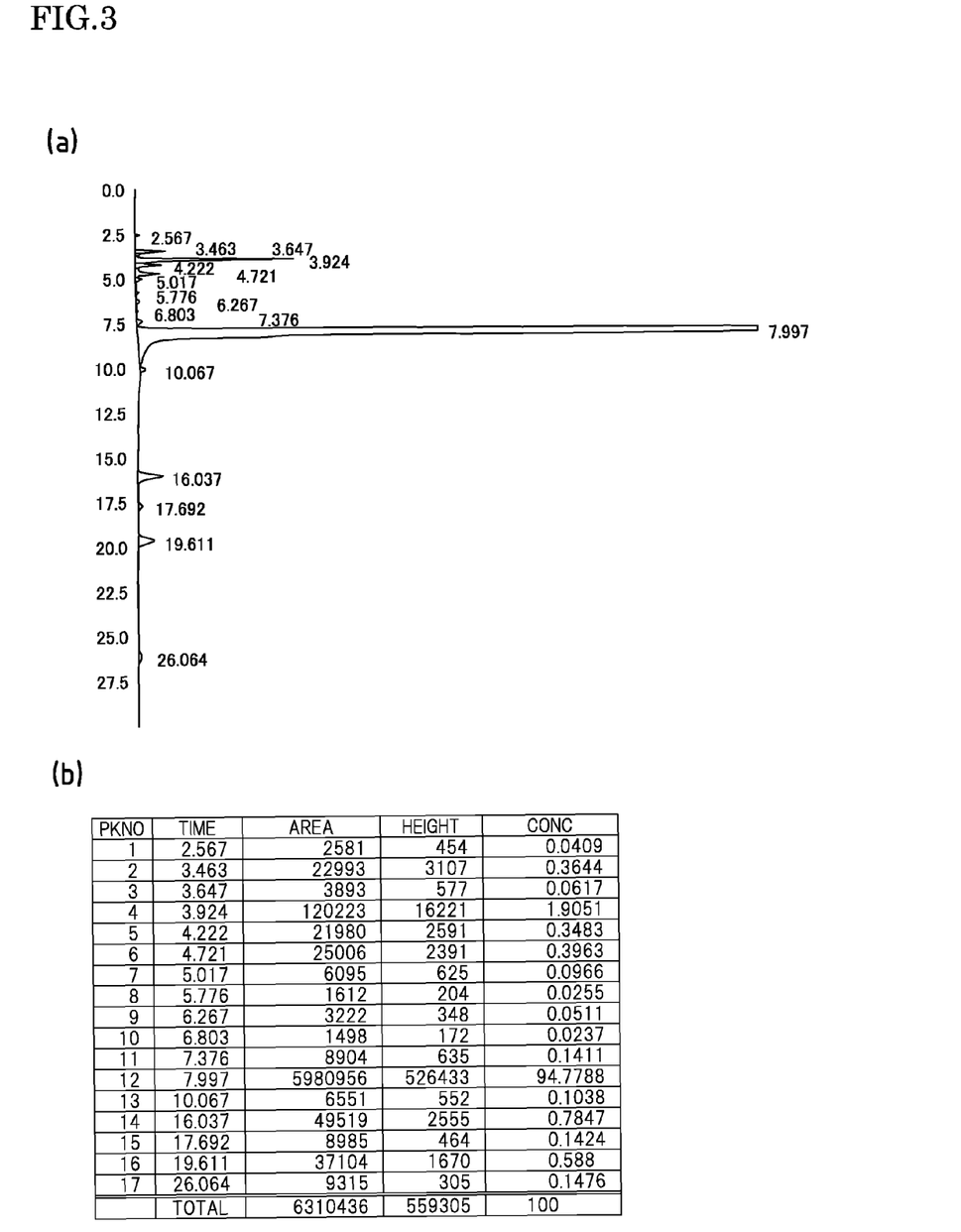
FIG. 3(a) is a chromatogram of the reaction solution in which the bis-(1(2)H-tetrazol-5-yl)amine metal salt compound of Example 6 according to the method for producing bis-(1(2)H-tetrazol-5-yl)amine of the present invention is dissolved.
FIG. 3(b) is analytical data of the chromatogram.

The reaction solution after cooling was subjected to HPLC analysis, and the results of which are presented in FIG. 3. The results of the analysis showed that the bis-(1(2)H-tetrazol-5-yl)amine metal salt compound in the resulting reaction solution had a purity of 94.0 area % or greater and a peak derived from an impurity appearing within the relative retention time starting at 1.08 and ending at 1.20 assuming that the retention time to the main peak is 1 accounting for 0.1 area % or less according to the area percentage obtained by the HPLC analysis. Thereafter, 31.4 g (0.202 mol) of a 63% sulfuric acid solution was added to the reaction solution for crystallization, and 2.0 g of a 40% aqueous sodium nitrite solution was then added to decompose unreacted hydrogen azide. Crystals were filtered off at about 25.degree. C., thereby giving about 49 g of wet bis-(1(2)H-tetrazol-5-yl)amine.

Figure 4:
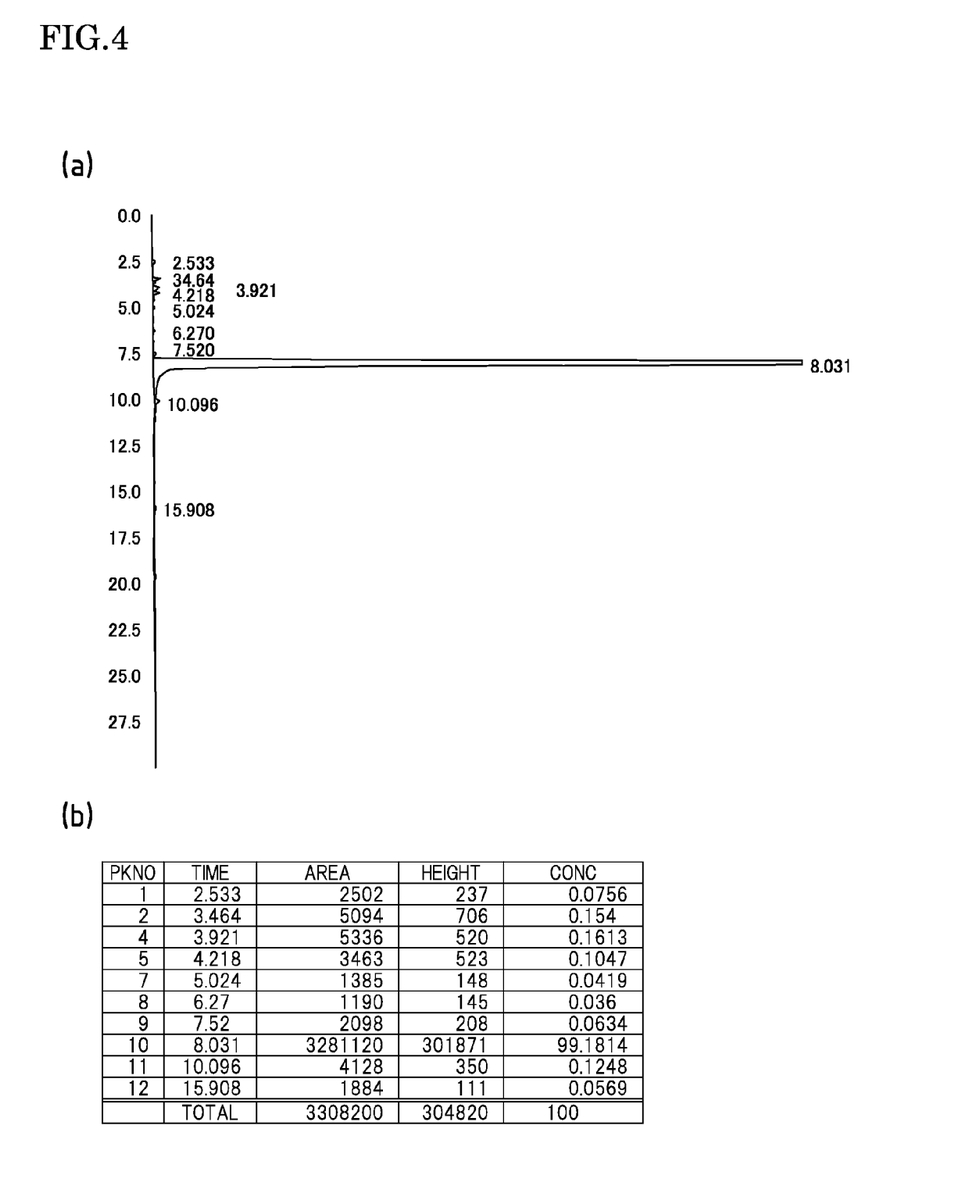
FIG. 4(a) is a chromatogram of the wet bis-(1(2)H-tetrazol-5-yl)amine of Example 6 according to the method for producing bis-(1(2)H-tetrazol-5-yl)amine of the present invention.
FIG. 4(b) is analytical data of the chromatogram.

The results of the HPLC analysis of the resulting wet bis-(1(2)H-tetrazol-5-yl)amine are presented in FIG. 4. The HPLC conditions were the same as those used in the HPLC analysis of the reaction solution described above. The results of the analysis showed that the wet bis-(1(2)H-tetrazol-5-yl)amine in the resulting reaction solution had a purity of 99.0 area % or greater and a peak derived from an impurity appearing within the relative retention time starting at 1.08 and ending at 1.20 assuming that the retention time to the main peak is 1 accounting for 0.1 area % or less according to the area percentage obtained by the HPLC analysis.

Thereafter, the entire amount of the wet bis-(1(2)H-tetrazol-5-yl)amine and 150 mL of water were introduced into a 200 mL flask to form a suspension. The pH was controlled so as to be 4 to 6 by adding a 28% ammonia solution. The suspension was cooled to 10° C. or lower and then subjected to filtration, thereby giving about 35 g of wet bis-(1(2)H-tetrazol-5-yl)amine ammonium salt.

Figure 5:
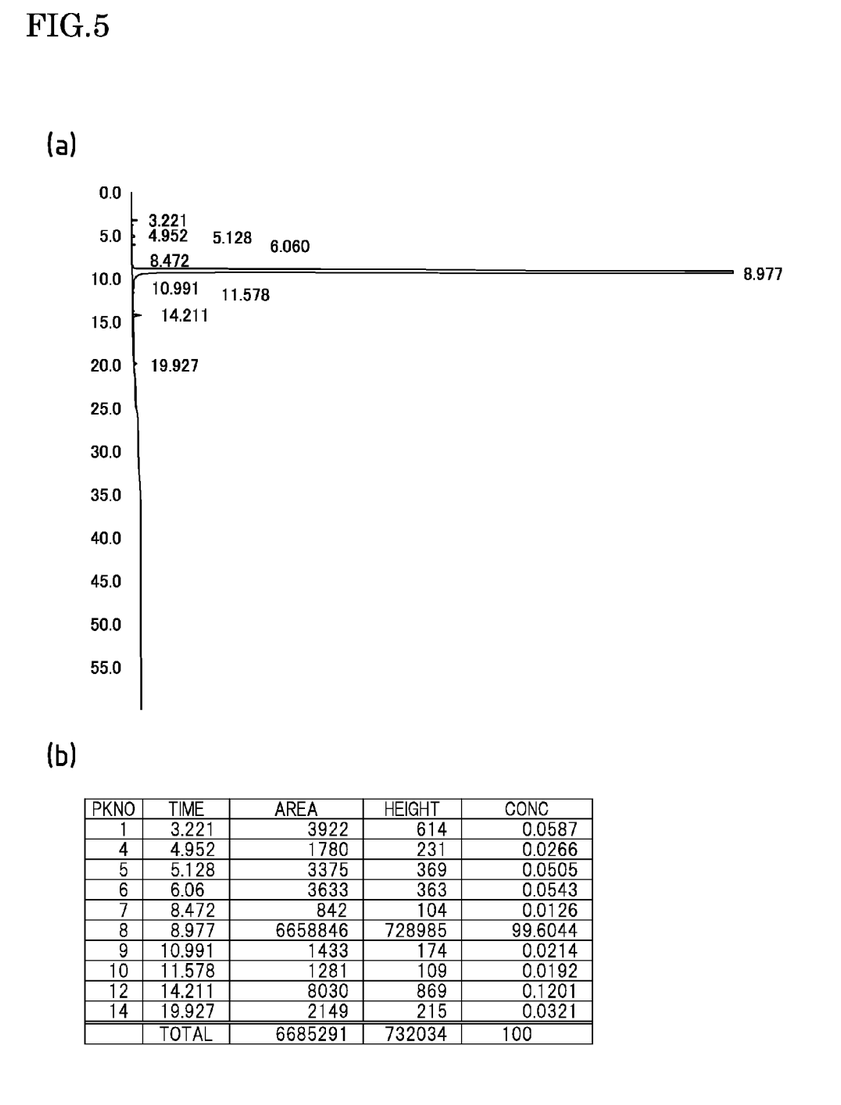

This compound was vacuum-dried at 60° C., thereby giving 29.2 g of bis-(1(2)H-tetrazol-5-yl)amine ammonium salt having a purity of 99.6 wt % on a weight basis as determined from the results of HPLC analysis in a yield of 86%. FIG. 5 shows the HPLC data obtained accordingly. Note that the HPLC conditions included detection with UV220 nm, a column of Inertsil ODS-3 having 4.6 mm ID.times.250 mm, a column bath temperature of 30° C., a mobile phase (solution A: 0.1% phosphoric acid solution/acetonitrile/methanol in a ratio of 950/25/25, and solution B: 0.1% phosphoric acid solution/acetonitrile in a ratio of 400/600), a gradient program (0-30 minutes: 100-50% solution A, 0-50% solution B, and 30-60 minutes: 50% solution A, 50% solution B), a mobile phase flow rate of 1.0 mL/min, and an amount of a sample injected of 20 μL (loop). The results of the analysis showed that the bis-(1(2)H-tetrazol-5-yl)amine ammonium salt in the resulting reaction solution had a purity of 99.0 wt % or greater and a peak derived from an impurity appearing within the relative retention time starting at 2.17 and ending at 2.24 assuming that the retention time to the main peak is 1 accounting for 0.1 wt % or less as determined on a weight basis according to the area percentage obtained by the HPLC analysis.

Comparative Example 1

Boric Acid 17.81 g (0.20 mol) of NaDCA, 26.00 g of sodium azide (0.40 mol, 2.0 times the molar amount of the entire NaDCA used in the reaction), 25.96 g of boric acid (0.42 mol, 1.05 times the chemical equivalents of the entire NaDCA used in the reaction), and 200 mL of water were introduced into a 300 mL flask and heated while stirring until the internal temperature reached 100° C.

While the internal temperature was maintained at 100° C., the reaction was promoted by stirring at 100° C. for 42 hours, and the internal temperature was then lowered to near room temperature.

48.3 g (0.312 mol) of a 63% sulfuric acid solution was added for crystallization, and 8.3 g of a 40% aqueous sodium nitrite solution was then added to decompose unreacted hydrogen azide. 2.06 g of a 63% sulfuric acid solution was further added, and then crystals were filtered off at about 25° C., thereby giving about 44.6 g of wet bis-(1(2)H-tetrazol-5-yl)amine.

This compound was vacuum-dried at 60° C., thereby giving 27.25 g of bis-(1(2)H-tetrazol-5-yl)amine having an HPLC purity of 77.5 area % in a yield of 79.6%.

Comparative Example 2

Conventional Method with the Use of Sulfuric Acid 17.81 g (0.20 mol) of NaDCA, 26.39 g of sodium azide (0.406 mol, 2.03 times the molar amount of the entire NaDCA used in the reaction), and 120 mL of water were introduced into a 300 mL flask and heated while stirring until the internal temperature reached 100° C.

While the internal temperature was maintained at 100° C., 16.81 g (0.108 mol) of 63% sulfuric acid was added over the course of 3 hours.

While the internal temperature was maintained at 100° C., the reaction was promoted by stirring for 10 hours, and the internal temperature was then lowered to near room temperature.

Figure 6:
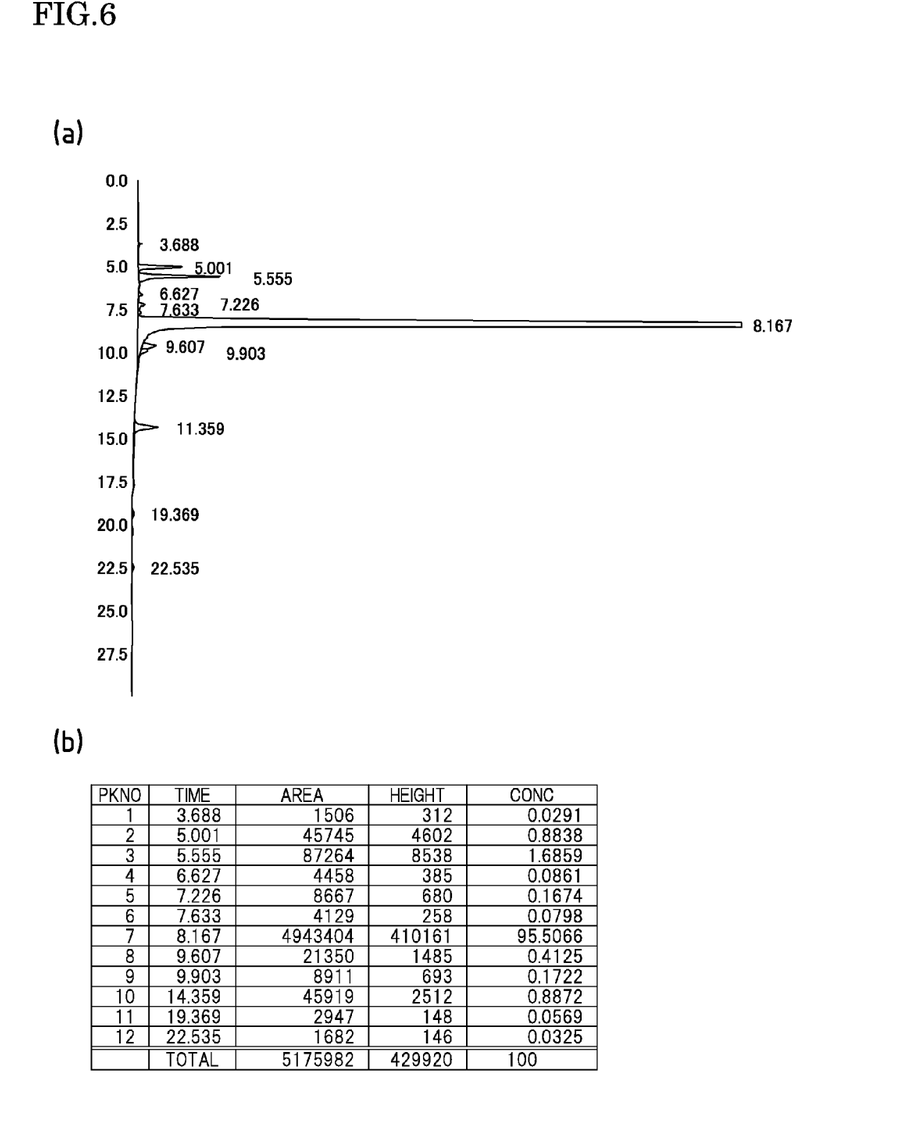
FIG. 6(a) is a chromatogram of the reaction solution in which the bis-(1(2)H-tetrazol-5-yl)amine metal salt compound of Comparative Example according to a conventional method for producing bis-(1(2)H-tetrazol-5-yl)amine is dissolved.
FIG. 6(b) is analytical data of the chromatogram.

The reaction solution after cooling was subjected to HPLC analysis, and the results of which are presented in FIG. 6.

The HPLC analysis conditions included detection with UV220 nm, a column of Inertsil ODS-3 (4.6 mm ID.times.250 mm), a column bath temperature of 40° C., a mobile phase of water/acetonitrile/phosphoric acid in a ratio of 800/200/0.1, a mobile phase flow rate of 0.7 mL/min, and an amount of sample injected of 10 μL (loop). The results of the analysis showed that the bis-(1(2)H-tetrazol-5-yl)amine metal salt compound in the resulting reaction solution had a purity of 94.0 area % or greater but a peak derived from an impurity appearing within the relative retention time starting at 1.08 and ending at 1.20 assuming that the retention time to the main peak is 1 accounting for 0.4 area % or greater according to the area percentage obtained by the HPLC analysis.

Thereafter, 75 mL of water and 31.45 g (0.202 mol) of a 63% sulfuric acid solution were added to the reaction solution for crystallization, and 2.0 g of a 40% aqueous sodium nitrite solution was then added to decompose unreacted hydrogen azide. Crystals were filtered off at about 25° C., thereby giving about 42 g of wet bis-(1(2)H-tetrazol-5-yl)amine.

Figure 7:
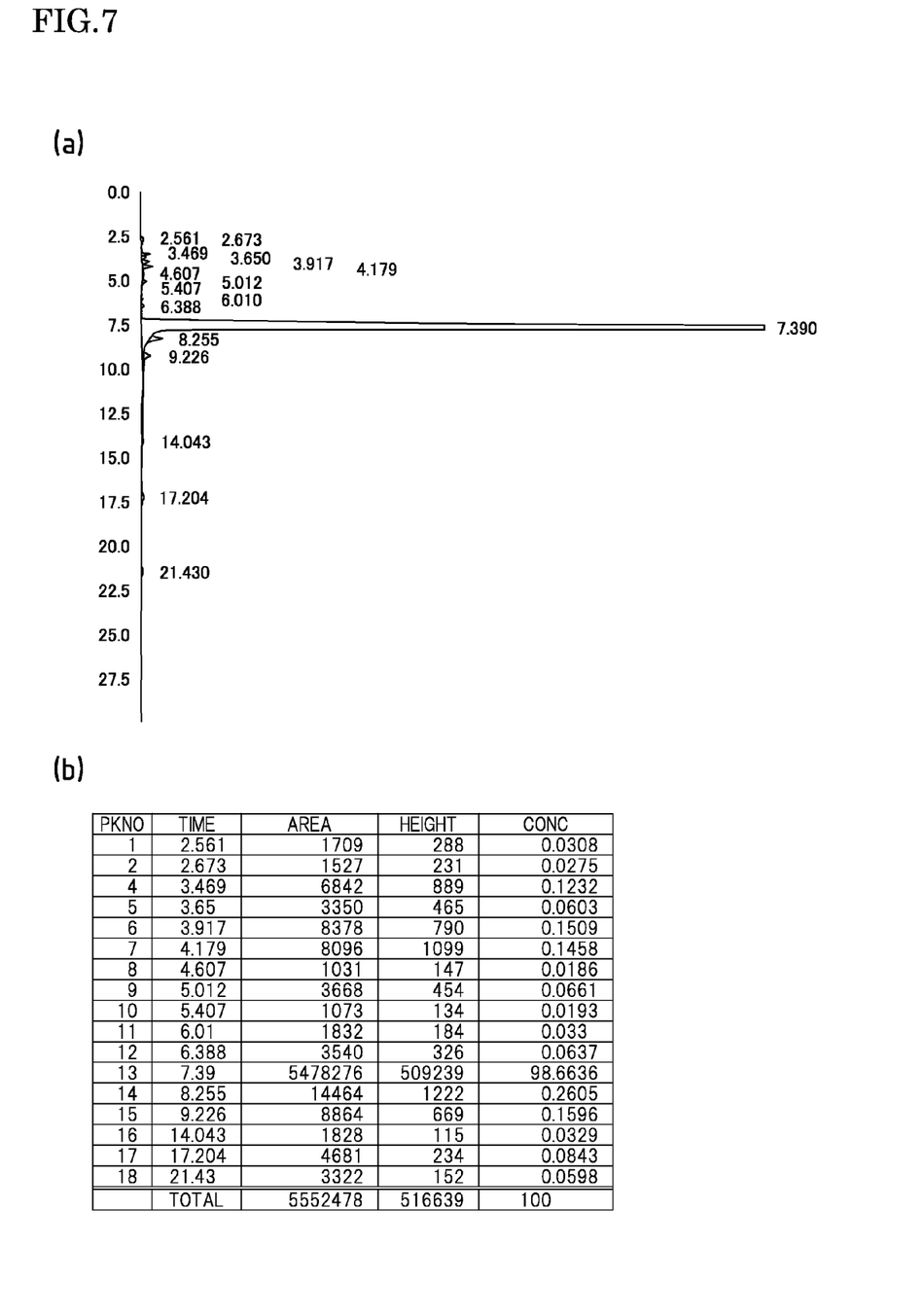
FIG. 7(a) is a chromatogram of the wet bis-(1(2)H-tetrazol-5-yl)amine of Comparative Example 2 according to a conventional method for producing bis-(1(2)H-tetrazol-5-yl)amine.
FIG. 7(b) is analytical data of the chromatogram.

The results of the HPLC analysis of the resulting wet bis-(1(2)H-tetrazol-5-yl)amine are presented in FIG. 7. The HPLC conditions were the same as those used in the HPLC analysis of the reaction solution described above. The results of the analysis showed that the wet bis-(1(2)H-tetrazol-5-yl)amine in the resulting reaction solution had a purity of 98.7 area % and a peak derived from an impurity appearing within the relative retention time starting at 1.08 and ending at 1.20 assuming that the retention time to the main peak is 1 accounting for 0.26 area % according to the area percentage obtained by the HPLC analysis.

Thereafter, the entire amount of the wet bis-(1(2)H-tetrazol-5-yl)amine and 150 mL of water were introduced into a 200 mL flask to form a suspension. The pH was controlled so as to be 4 to 6 by adding a 28% ammonia solution. The suspension was cooled to 10° C. or lower and then subjected to filtration, thereby giving about 32 g of wet bis-(1(2)H-tetrazol-5-yl)amine ammonium salt.

Figure 8:
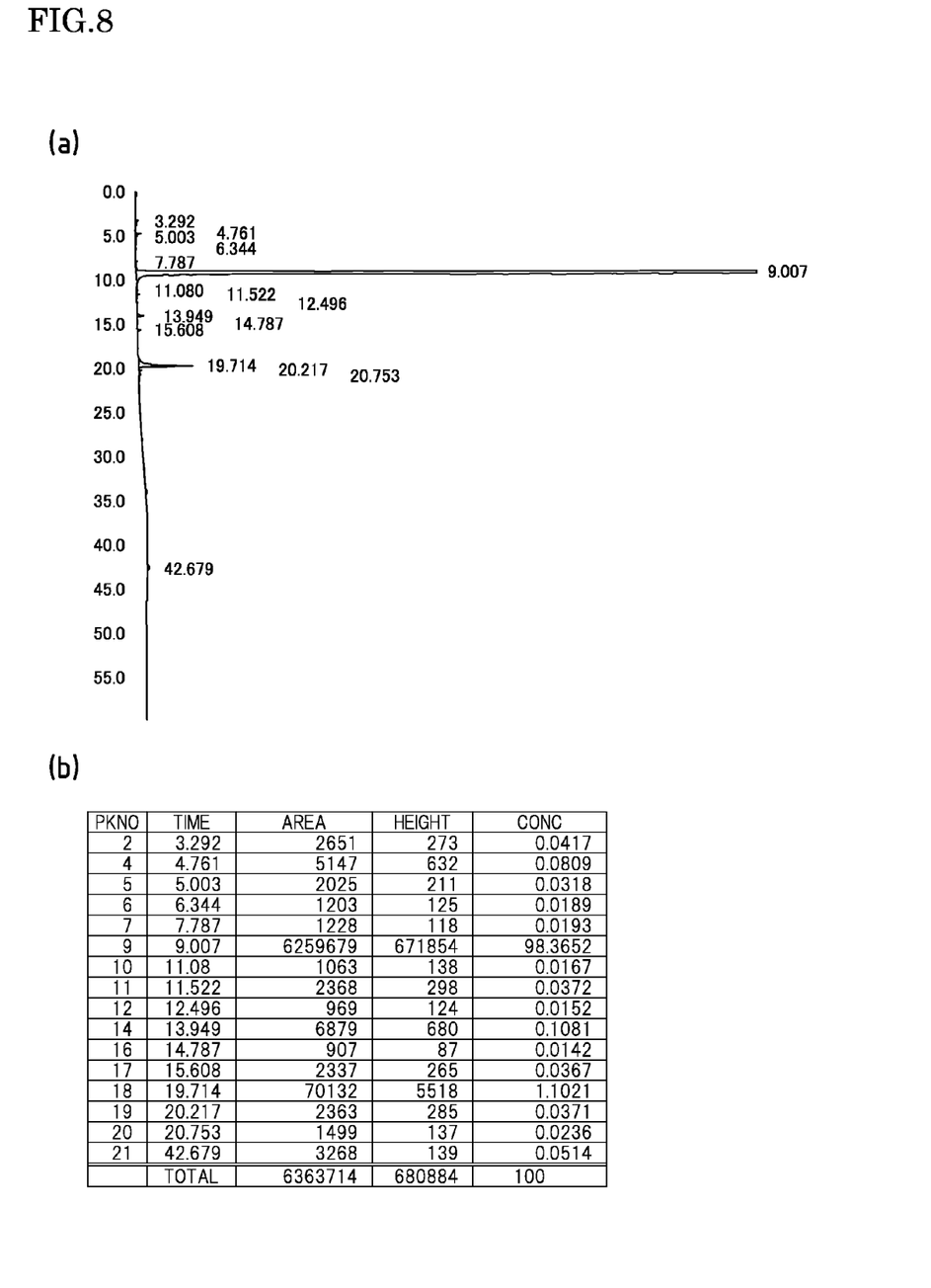
FIG. 8(a) is a chromatogram of the bis-(1(2)H-tetrazol-5-yl)amine ammonium salt of Comparative Example 2 according to a conventional method for producing bis-(1(2)H-tetrazol-5-yl)amine.
FIG. 8(b) is analytical data of the chromatogram.

This compound was vacuum-dried at 60° C., thereby giving 28.8 g of a bis-(1(2)H-tetrazol-5-yl)amine ammonium salt having a purity of 98.4 wt % as determined on a weight basis according to the area percent obtained by the HPLC analysis in a yield of 84.8%. FIG. 8 shows the HPLC data obtained accordingly. Note that the HPLC conditions included detection with UV220 nm, a column of Inertsil ODS-3 having 4.6 mm ID.times.250 mm, a column bath temperature of 30° C., a mobile phase (solution A: 0.1% phosphoric acid solution/acetonitrile/methanol in a ratio of 950/25/25, and solution B: 0.1% phosphoric acid solution/acetonitrile in a ratio of 400/600), a gradient program (0-30 minutes: 100-50% solution A, 0-50% solution B, and 30-60minutes: 50% solution A, 50% solution B), a mobile phase flow rate of 1.0 mL/min, and an amount of a sample injected of 20 μL (loop). The results of the analysis showed that the bis-(1(2)H-tetrazol-5-yl)amine ammonium salt in the resulting reaction solution had a purity of 99.0 wt % or less and a peak derived from an impurity appearing within the relative retention time starting at 2.17 and ending at 2.24 assuming that the retention time to the main peak is 1 accounting for 1.1 wt % or greater as determined on a weight basis according to the area percentage obtained by the HPLC analysis.

INDUSTRIAL APPLICABILITY

The present invention is useful in producing a bis-(1(2)H-tetrazol-5-yl)amine compound that exhibits excellent properties as a gas generant for air-bags and as a foaming agent.

Description of Abbreviations

IM1, IM2, and IM3: intermediates
NaDCA: dicyanamide salt
BTA-2Na: bis-(1(2)H-tetrazol-5-yl)amine metal salt compound

What is claimed is:

1. A method for producing bis-(1(2)H-tetrazol-5-yl)amine ammonium salt comprising the steps of:
   heating to 50 to 120° C. a solution mixture in which an azide salt in a necessary amount and a dicyanamide salt in an amount corresponding to 1 to 80 wt% of a necessary amount are added to a solvent,
   adding an acid in an amount of 1.54 to 2.22 chemical equivalents of the dicyanamide salt in the solution mixture to carry out a reaction at 50 to 120° C,
   adding an acid and a dicyanamide salt solution in which remaining dicyanamide salt is dissolved in a solvent to promote the reaction,
   heat-treating at 75° C. or greater the obtained metal salt compound,
   adding a solution of a second acid to form at least one of bis-(1(2)H-tetrazol-5-yl)amine anhydrate and monohydrate, and
   adding an amine to the obtained at least one of bis-(1(2)H-tetrazol-5-yl)amine anhydrate and monohydrate to convert the at least one of bis-(1(2)H-tetrazol-5-yl)amine anhydrate and monohydrate into bis-(1(2)H-tetrazol-5-yl)amine ammonium salt,
wherein the bis-(1(2)H-tetrazol-5-yl)amine ammonium salt has a purity of 99.0 wt% or greater on a weight basis and not showing a peak accounting for 0.1 wt% or greater on a weight basis within a relative retention time starting at 2.17 and ending at 2.24 assuming that a retention time to a main peak is 1 as determined according to an area percentage obtained by HPLC analysis,
provided that HPLC analysis conditions include:
   detection with UV220 nm,
   a column of Inertsil ODS-3 having 4.6 mm ID×250 mm,
   a column bath temperature of 30° C.,
   a mobile phase of:
   solution A: 0.1% phosphoric acid solution/acetonitrile/methanol in a ratio of 950/25/25, and
   solution B: 0.1% phosphoric acid solution/acetonitrile in a ratio of 400/600,
   a gradient program of:
   0-30 minutes: 100-50% solution A, 0-50% solution B,
   30-60 minutes: 50% solution A, 50% solution B;
   a mobile phase flow rate of 1.0 mL/min, and
   an amount of a sample injected of 20 μL (loop).

* * * * *